US 10,292,774 B2

(12) United States Patent
McDonell

(10) Patent No.: US 10,292,774 B2
(45) Date of Patent: May 21, 2019

(54) BONE AND TOOL TRACKING WITH OPTICAL WAVEGUIDE MODELING SYSTEM IN COMPUTER-ASSISTED SURGERY USING PATIENT-ATTACHED MULTICORE OPTICAL FIBER

(71) Applicant: ZIMMER, INC., Warsaw, IN (US)

(72) Inventor: Matthew J. McDonell, Fort Wayne, IN (US)

(73) Assignee: ZIMMER, INC., Warsaw, IN (US)

( * ) Notice: Subject to any disclaimer, the term of this patent is extended or adjusted under 35 U.S.C. 154(b) by 0 days.

(21) Appl. No.: 16/048,225

(22) Filed: Jul. 28, 2018

(65) Prior Publication Data
US 2019/0029759 A1 Jan. 31, 2019

Related U.S. Application Data

(60) Provisional application No. 62/538,533, filed on Jul. 28, 2017.

(51) Int. Cl.
A61B 34/20 (2016.01)
G02B 6/02 (2006.01)
A61B 34/30 (2016.01)

(52) U.S. Cl.
CPC .............. A61B 34/20 (2016.02); A61B 34/30 (2016.02); G02B 6/02042 (2013.01); G02B 6/02057 (2013.01); A61B 2034/2055 (2016.02)

(58) Field of Classification Search
CPC . A61B 34/20; A61B 34/30; A61B 2034/2055; G02B 6/02057; G02B 6/02042
See application file for complete search history.

(56) References Cited

U.S. PATENT DOCUMENTS

| 8,241,296 B2* | 8/2012 | Wasielewski | A61B 17/00 606/96 |
| 9,050,131 B2 | 6/2015 | Van Vorhis et al. | |
| 9,066,739 B2 | 6/2015 | Larkin | |
| 10,124,124 B2* | 11/2018 | Couture | A61M 5/427 |
| 10,136,952 B2* | 11/2018 | Couture | A61B 34/10 |
| 10,143,526 B2* | 12/2018 | Walker | A61B 34/37 |
| 2002/0087101 A1 | 7/2002 | Barrick et al. | |

(Continued)

FOREIGN PATENT DOCUMENTS

WO 2016038489 5/2016

Primary Examiner — Andrew Jordan
(74) Attorney, Agent, or Firm — Norton Rose Fulbright Canada LLP

(57) ABSTRACT

There is described a method for tracking a patient in a coordinate system of a surgical tool using an optical waveguide modeling system having one multicore optical fiber with a portion attached to the surgical tool and a portion attached to the patient. The method generally includes receiving a patient model representing a shape and orientation of at least one of a limb and a bone of the patient, generating a waveguide model representing a shape and orientation of the multicore optical fiber as attached to the surgical tool and to the patient, and tracking the patient model in the coordinate system by registering the patient model in the coordinate system using the waveguide model and known spatial relationships relating to the surgical tool, the portion of the multicore optical fiber attached to the surgical tool, and the portion of the multicore optical fiber attached to the patient.

21 Claims, 10 Drawing Sheets

(56) References Cited

U.S. PATENT DOCUMENTS

| | | | |
|---|---|---|---|
| 2009/0314925 A1* | 12/2009 | Van Vorhis | A61B 34/20 |
| | | | 250/203.2 |
| 2010/0030063 A1 | 2/2010 | Lee | |
| 2017/0151027 A1* | 6/2017 | Walker | A61B 34/37 |
| 2017/0360512 A1* | 12/2017 | Couture | A61B 34/10 |

* cited by examiner

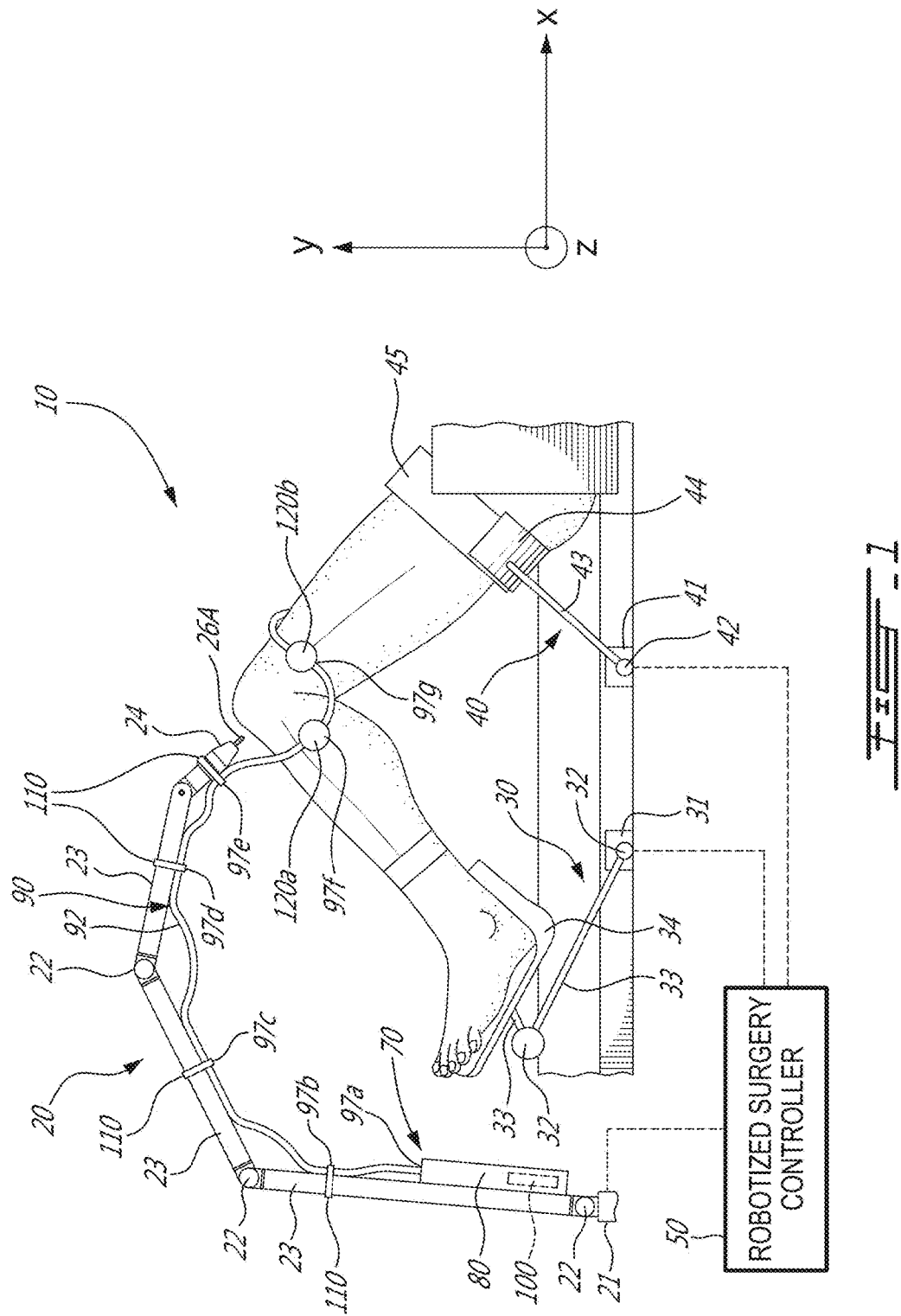

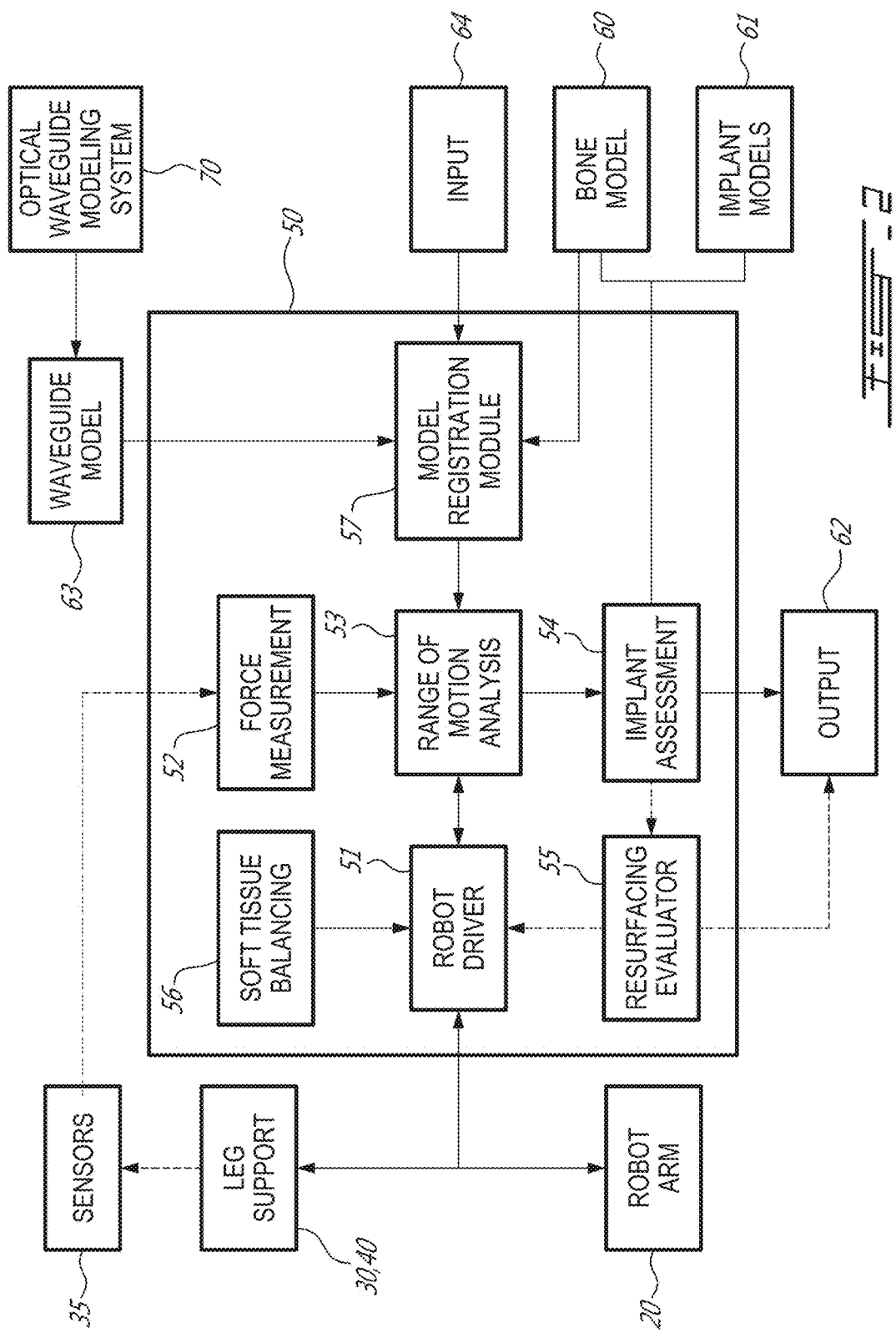

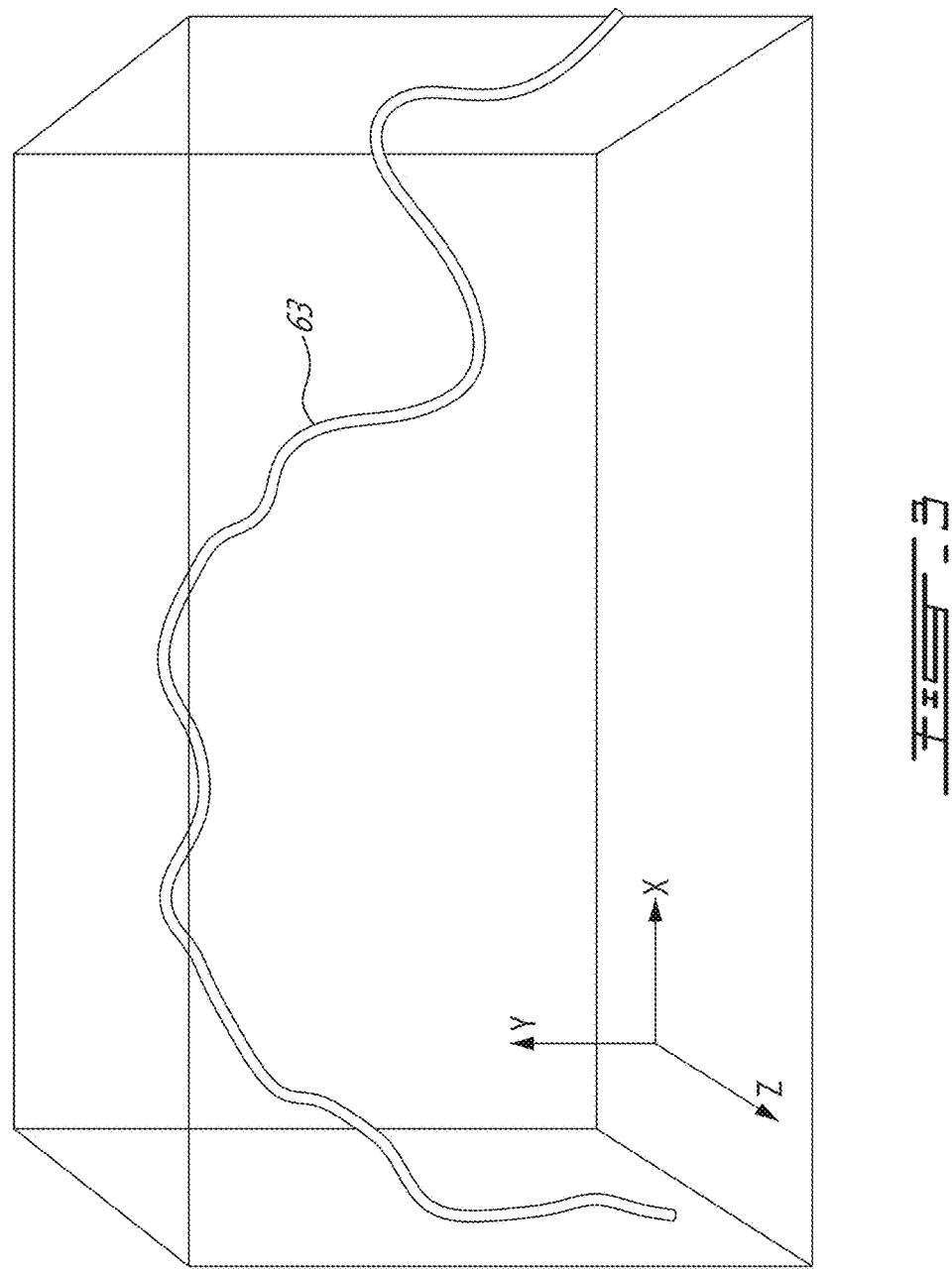

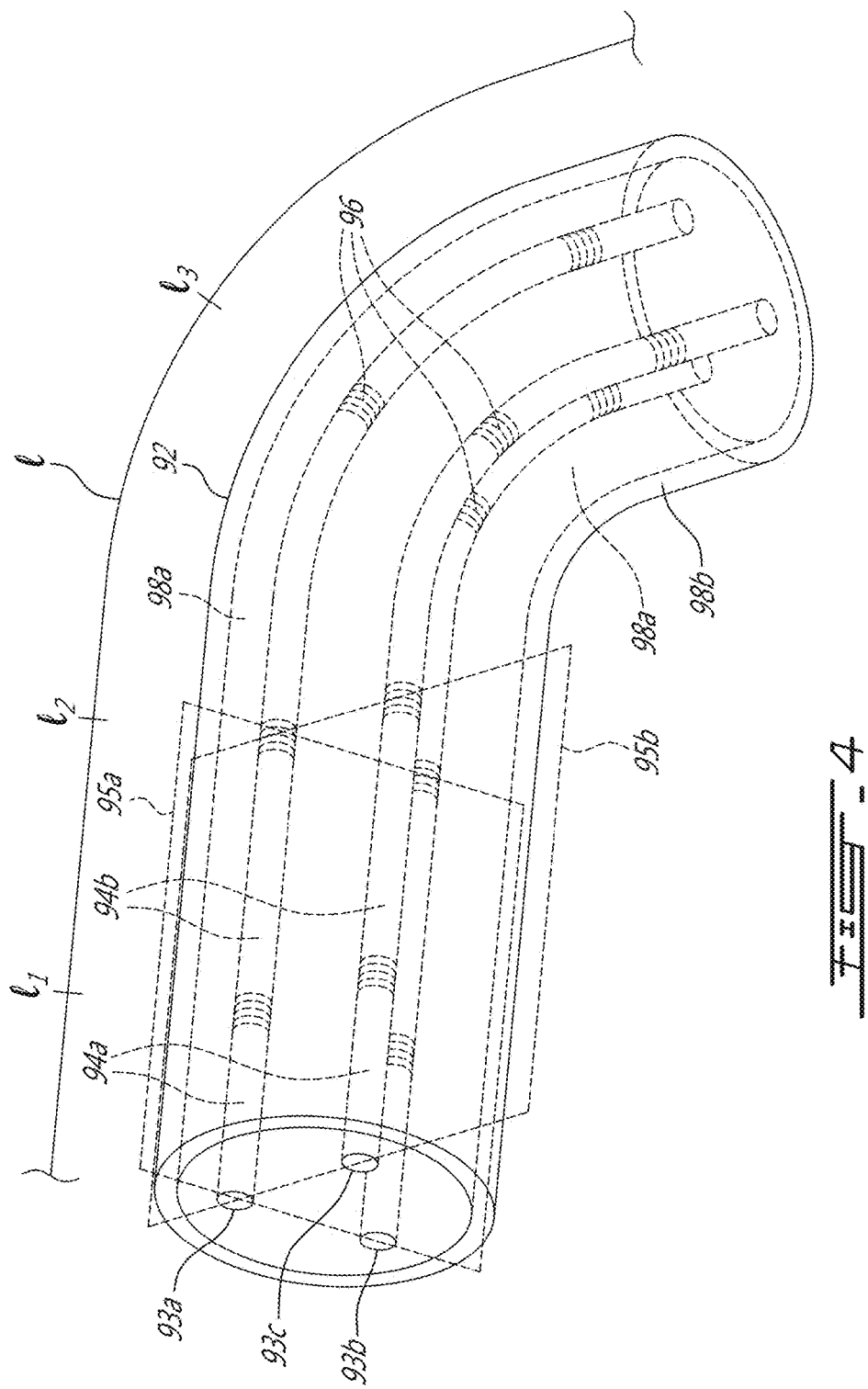

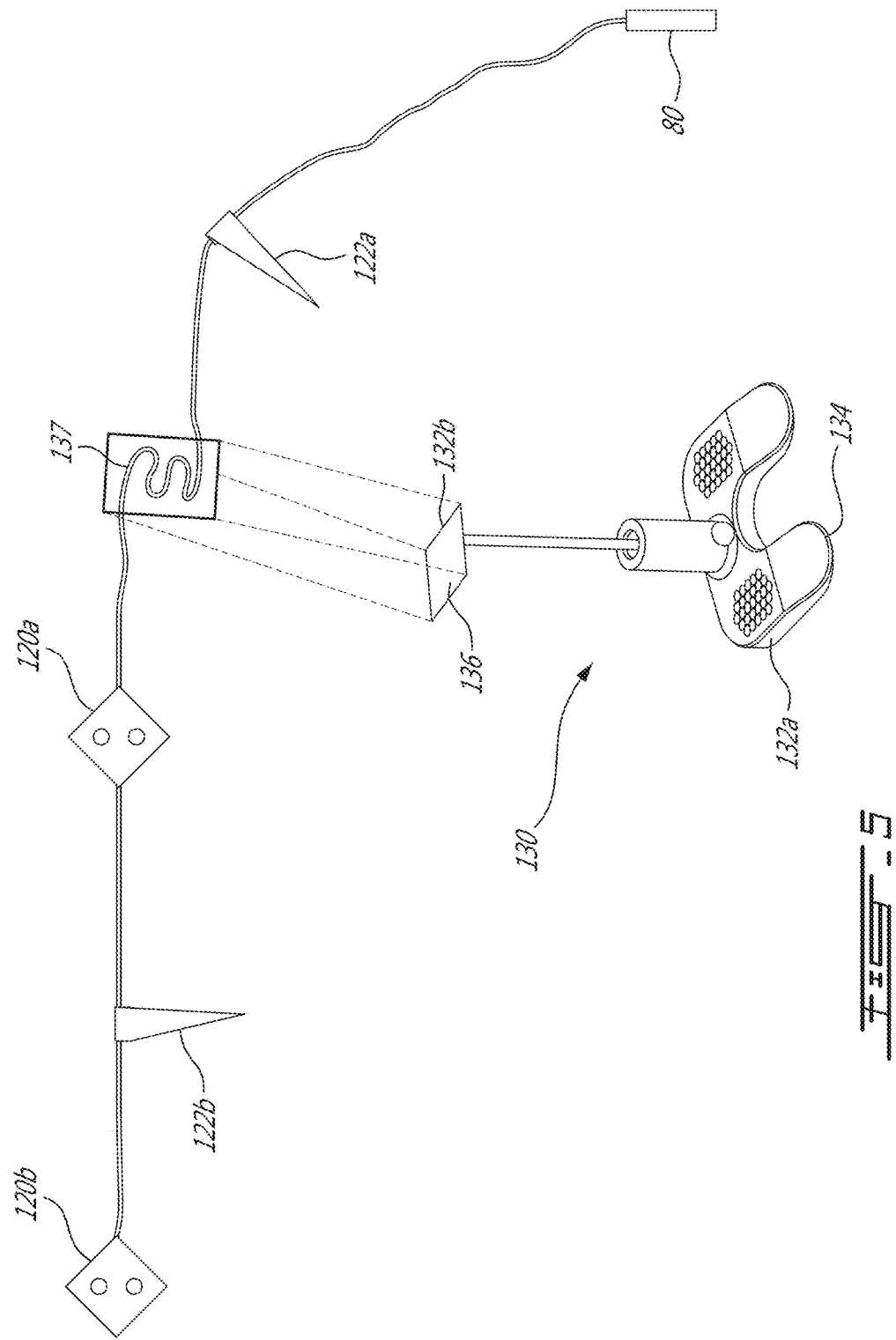

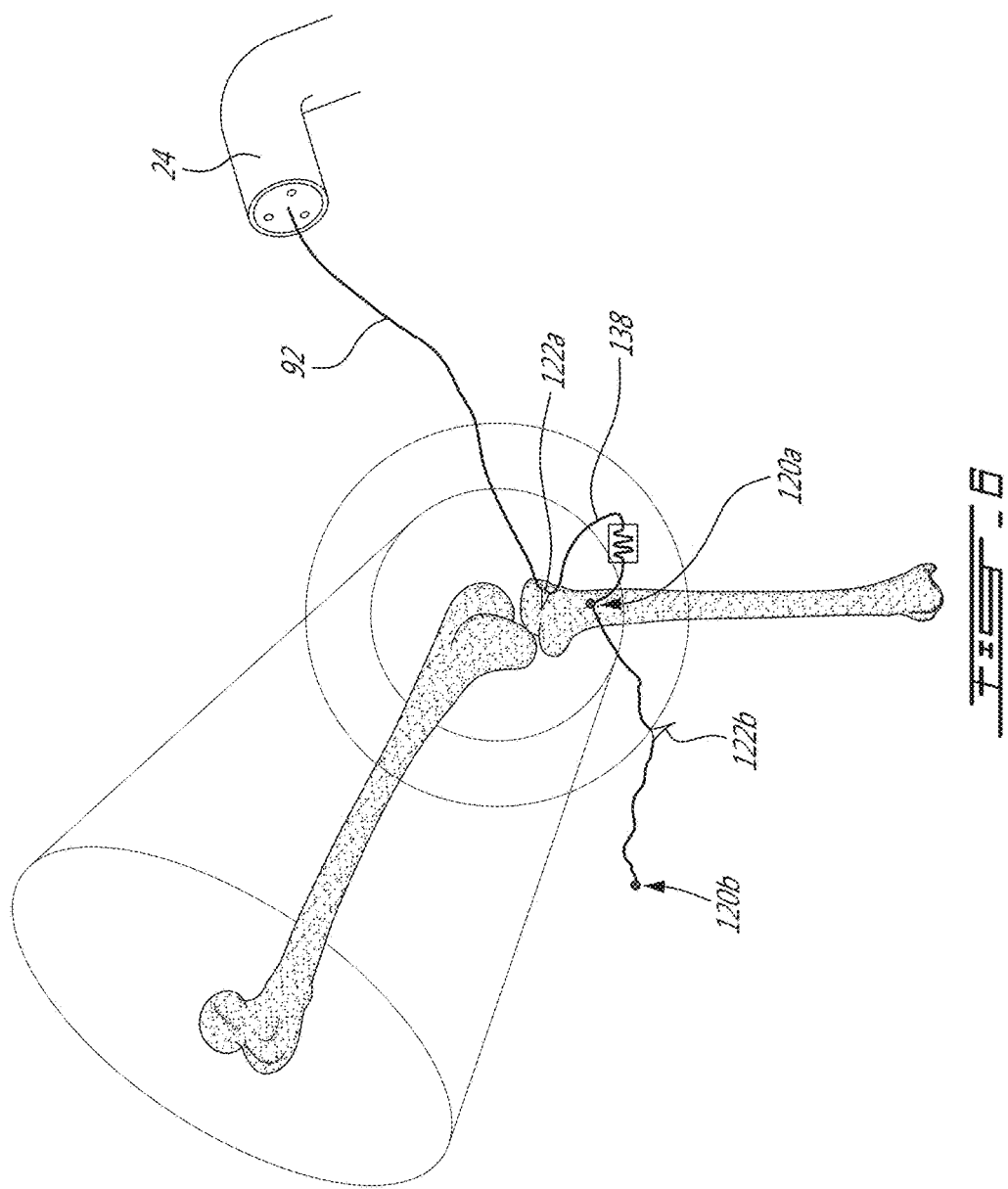

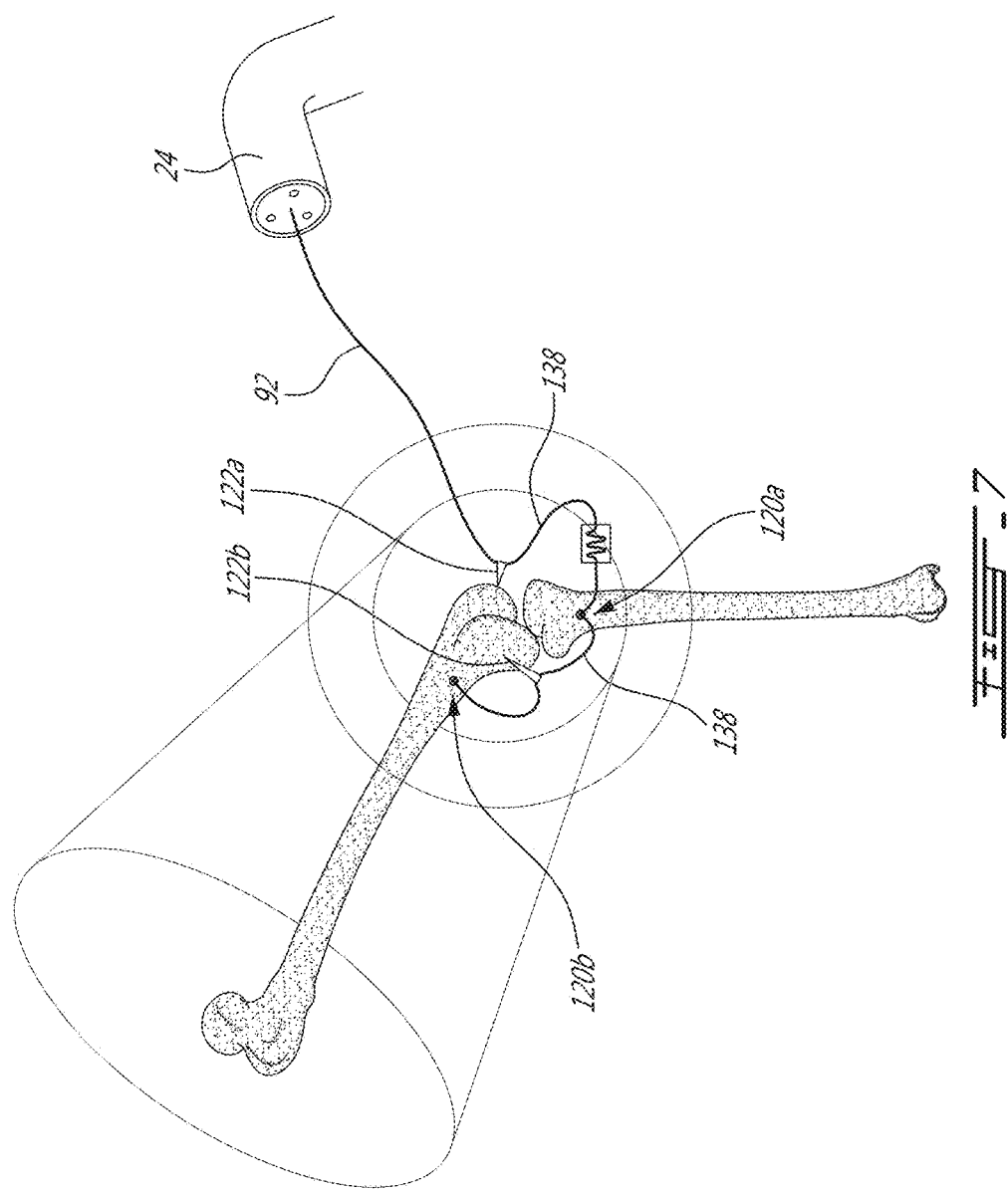

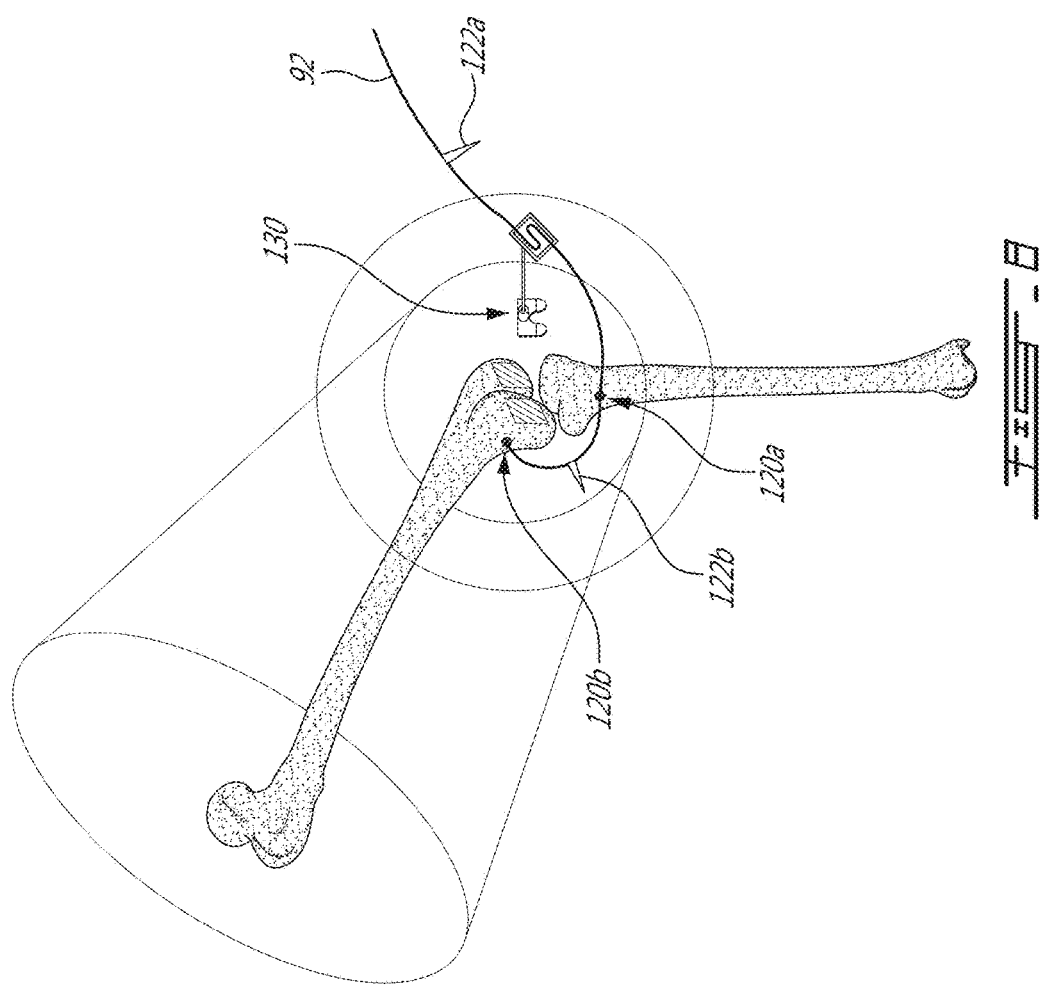

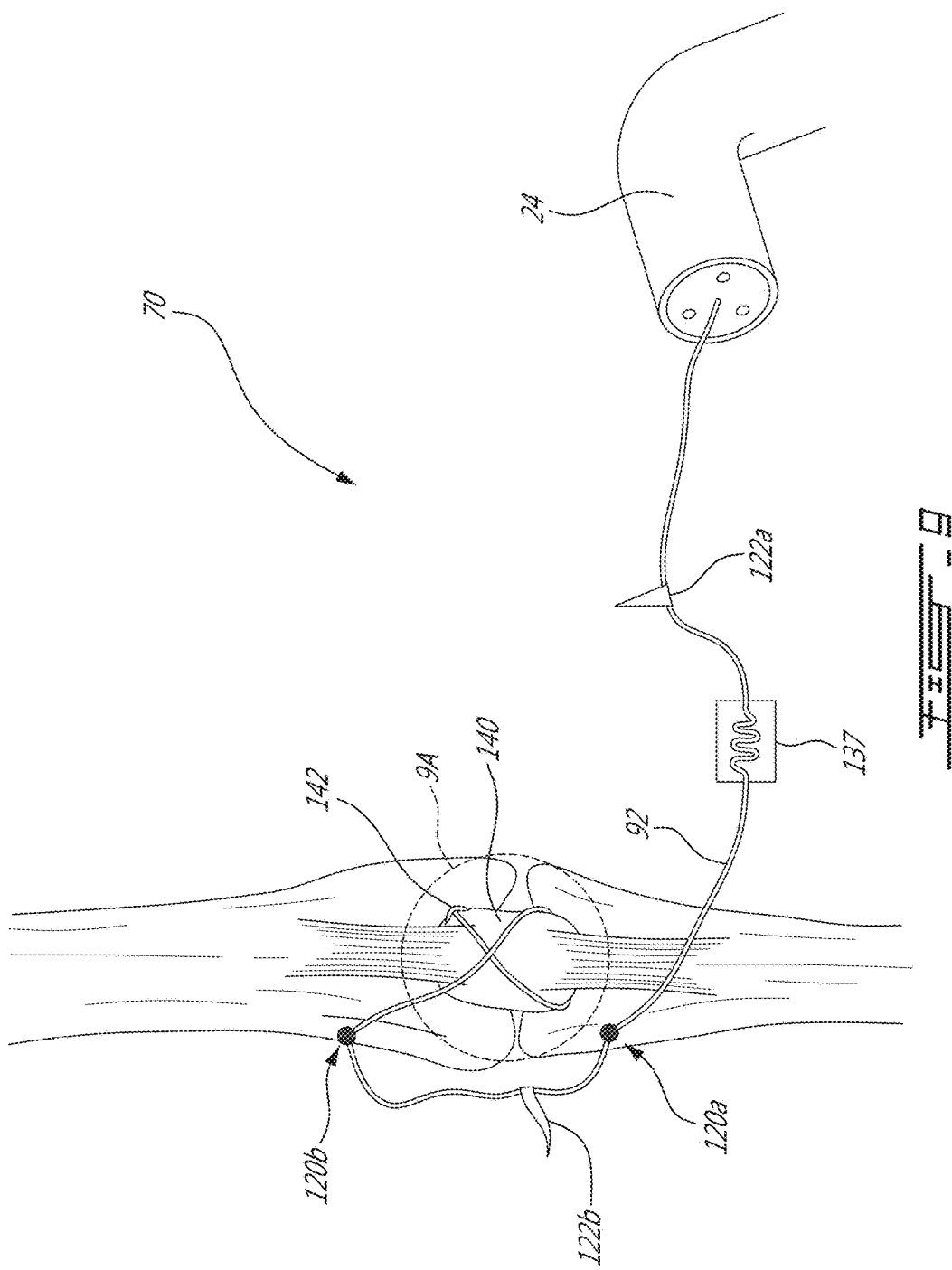

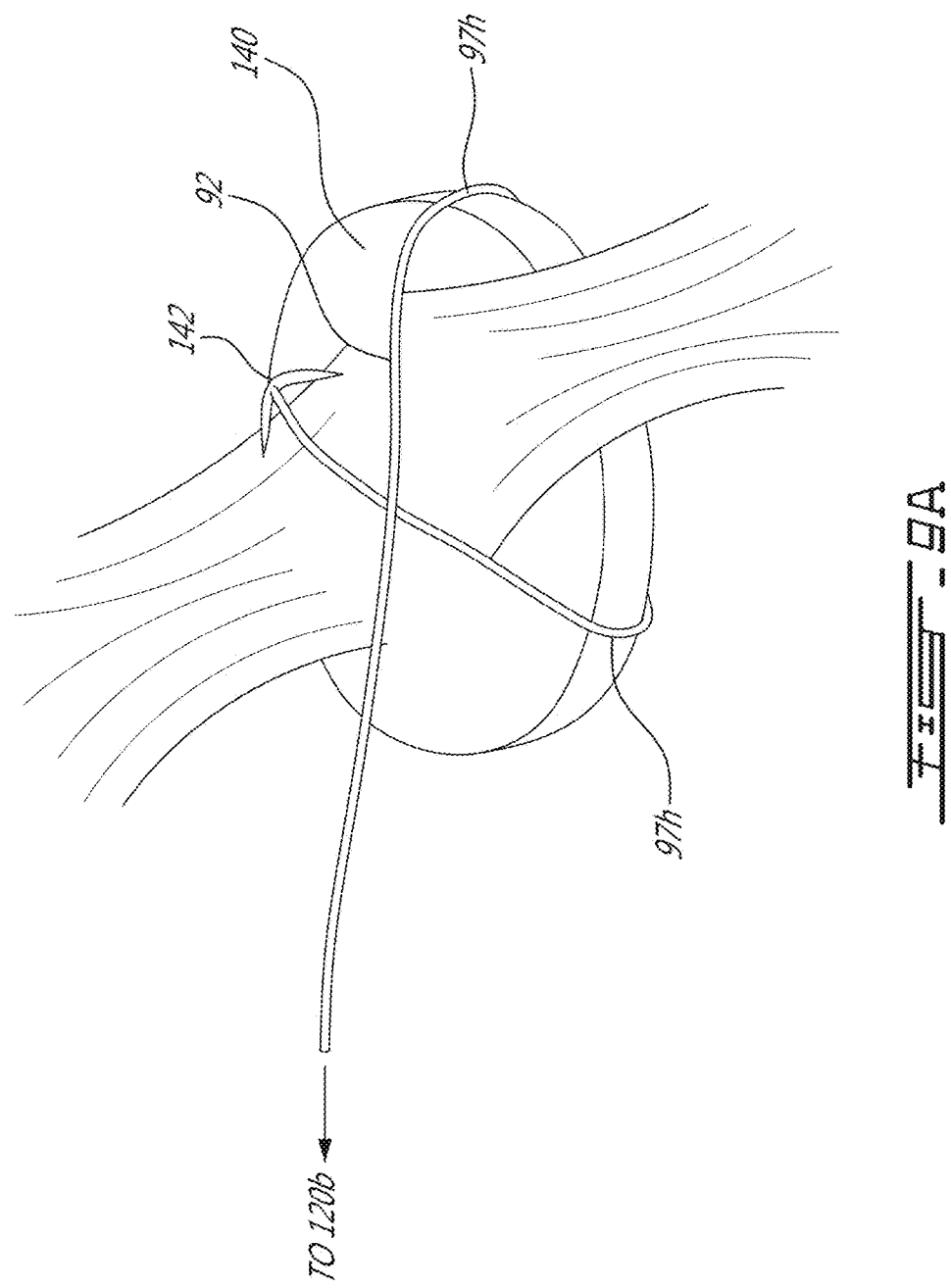

BONE AND TOOL TRACKING WITH OPTICAL WAVEGUIDE MODELING SYSTEM IN COMPUTER-ASSISTED SURGERY USING PATIENT-ATTACHED MULTICORE OPTICAL FIBER

CROSS-REFERENCE TO RELATED APPLICATIONS

The present application claims priority to U.S. Provisional Patent Application No. 62/538,533 filed Jul. 28, 2017, the entire contents of which are incorporated herein by reference.

TECHNICAL FIELD

The present application relates to computer-assisted orthopedic surgery involving the tracking of bones and tools to guide an operator or robot in performing accurate and precise bone alterations in surgery.

BACKGROUND

Computer-assisted surgery has been developed in order to help an operator in altering bones, and in positioning and orienting implants to a desired location. Among the various tracking technologies used in computer-assisted surgery, optical navigation, C-arm validation and manual reference guides have been used. The optical navigation requires the use of a navigation system, which adds operative time. Moreover, it is bound to line-of-sight constraints which hamper the normal surgical flow. C-arm validation requires the use of bulky equipment and the validation is not cost-effective.

Such tracking technologies often assist an operator or surgeon while performing manual work. While surgeons may have developed an expertise in manipulations performed during surgery, some practitioners prefer the precision and accuracy of robotized intervention. However, the robotic equipment may be viewed as voluminous, also causing some line-of-sight issues. There exists room for improvement.

SUMMARY

It is therefore an aim of the present disclosure to provide an improved bone and tool tracking system and method.

In accordance with the present disclosure, there is provided a method for tracking a patient in a coordinate system of a surgical tool using an optical waveguide modeling system, the optical waveguide modeling system having at least one multicore optical fiber with at least one portion attached to the surgical tool and at least one portion attached to the patient, the method comprising: receiving a patient model representing a shape and orientation of at least one of a limb and a bone of the patient; generating a waveguide model representing a shape and orientation of the multicore optical fiber as attached to the surgical tool and to the patient; and tracking the patient model in the coordinate system of the surgical tool by registering the patient model in the coordinate system of the surgical tool using the waveguide model, a known spatial relationship between the surgical tool and the at least one portion of the multicore optical fiber attached to the surgical tool and a known spatial relationship between the patient and the at least one portion of the multicore optical fiber attached to the patient.

In accordance with the present disclosure, there is also provided a method for tracking a patient in a coordinate system of a surgical tool using an optical waveguide modeling system, the optical waveguide modeling system having at least one multicore optical fiber with at least one portion attached to the surgical tool and at least one portion attached to the patient, the method comprising: using a controller, receiving a patient model representing a shape and orientation of at least one of a limb and a bone of the patient; generating a waveguide model representing a shape and orientation of the multicore optical fiber as attached to the surgical tool and to the patient; and tracking the patient model in the coordinate system of the surgical tool by registering the patient model in the coordinate system of the surgical tool using the waveguide model, a known spatial relationship between the surgical tool and the at least one portion of the multicore optical fiber attached to the surgical tool and a known spatial relationship between the patient and the at least one portion of the multicore optical fiber attached to the patient.

In accordance with the present disclosure, there is further provided a computer-assisted surgery system for tracking a tool with respect to a bone of a patient, comprising: a patient model representing a shape and orientation of the bone of the patient; a surgical tool in communication with the computer-assisted surgery system; an optical waveguide modeling system having a multicore optical fiber; one or more limb attachments provided at one or more known positions along the multicore optical fiber; and one or more registration pointer provided at one or more known positions along the multicore optical fiber.

It will be understood that the expression "computer" as used herein is not to be interpreted in a limiting manner. It is rather used in a broad sense to generally refer to the combination of some form of one or more processing units and some form of memory system accessible by the processing unit(s). Similarly, the expression "controller" as used herein is not to be interpreted in a limiting manner but rather in a general sense of a device, or of a system having more than one device, performing the function(s) of controlling one or more devices.

It will be understood that the various functions of a computer or of a controller can be performed by hardware or by a combination of both hardware and software. For example, hardware can include logic gates included as part of a silicon chip of the processor. Software can be in the form of data such as computer-readable instructions stored in the memory system. With respect to a computer, a controller, a processing unit, or a processor chip, the expression "configured to" relates to the presence of hardware or a combination of hardware and software which is operable to perform the associated functions.

BRIEF DESCRIPTION OF THE DRAWINGS

FIG. 1 is a schematic view of an example of a robotized surgery system having an optical waveguide modeling system, in accordance with an embodiment;

FIG. 2 is a block diagram of an example of a robotized surgery controller used with the robotized surgery system of FIG. 1;

FIG. 3 is a graph representing a waveguide model of a multicore optical fiber of the optical waveguide modeling system of FIG. 1;

FIG. 4 is an enlarged view of a portion of a multicore optical fiber of the optical waveguide modeling system of FIG. 1;

FIG. 5 is a schematic view of an example of an optical waveguide modeling system, shown with a cut plane validation tool;

FIG. 6 is a schematic view of the optical waveguide modeling system of FIG. 5, with a first portion of a multicore optical fiber being attached to a tibia via a first bone attachment;

FIG. 7 is a schematic view of the optical waveguide modeling system of FIG. 5, with a second portion of the multicore optical fiber being further attached to a femur location via a second bone attachment;

FIG. 8 is a schematic view of the optical waveguide modeling system of FIG. 5, with a cut plane validation tool positioned on a first cut plane;

FIG. 9 is a schematic view of the optical waveguide modeling system of FIG. 5 with a given portion of the multicore optical fiber being wrapped around a patella; and FIG. 9A is an enlarged view of the multicore optical fiber wrapped around the patella of FIG. 9.

DETAILED DESCRIPTION

Referring to the drawings and more particularly to FIG. 1, a robotized surgery system is generally shown at 10, and is used to perform orthopedic surgery maneuvers on a patient, including pre-operative analysis of range of motion and implant assessment planning, as described hereinafter. The system 10 is shown relative to a patient's knee joint in supine decubitus, but only as an example. The system 10 could be used for other body parts, including non-exhaustively hip joint, spine, and shoulder bones. A particular function of the robotized surgery system 10 is assistance in planning soft tissue balancing, whereby the robotized surgery system 10 may be used in total knee replacement surgery, to balance tension/stress in knee joint ligaments.

The robotized surgery system 10 has a robot arm 20, a foot support 30, a thigh support 40 and a robotized surgery controller 50:

The robot arm 20 is the working end of the system 10, and is used to perform bone alterations as planned by an operator and/or the robotized surgery controller 50 and as controlled by the robotized surgery controller 50;

The foot support 30 supports the foot and lower leg of the patient, in such a way that it is only selectively movable. The foot support 30 is robotized in that its movements can be controlled by the robotized surgery controller 50;

The thigh support 40 supports the thigh and upper leg of the patient, again in such a way that it is only selectively or optionally movable. The thigh support 40 may optionally be robotized in that its movements can be controlled by the robotized surgery controller 50;

The robotized surgery controller 50 controls the robot arm 20, the foot support 30, and/or the thigh support 40. Moreover, as described hereinafter, the robotized surgery controller 50 may perform a range-of-motion (ROM) analysis and implant assessment in pre-operative planning, with or without the assistance of an operator; and The optical waveguide modeling (OWM) system 70 is used to track the robot arm 20 and the patient limb(s) or bone(s). More specifically, the OWM system 70 assists in performing the calibration of the patient bone with respect to the robot arm 20, for subsequent navigation in the X, Y, Z coordinate system. The OWM system 70 may also be used in non-robotized surgery as well.

Referring to FIG. 1, a schematic example of the robot arm 20 is provided. The robot arm 20 may stand from a base 21, for instance in a fixed relation relative to the operating-room or table supporting the patient in some specific embodiments. Indeed, the relative positioning of the robot arm 20 relative to the patient is a determinative factor in the precision of the surgical procedure, whereby the foot support 30 and thigh support 40 may assist in keeping the operated limb fixed in the illustrated X, Y, Z coordinate system. However, it will be appreciated that the fixed relation between the base 21 and operating-room or table is only optional, as will be described below. The robot arm 20 has a plurality of joints 22 and links 23, of any appropriate form, to support a tool head 24 that interfaces with the patient. The arm 20 is shown being a serial mechanism, arranged for the tool head 24 to be displaceable in sufficient degrees of freedom (DOF). For example, the robot arm 20 controls 6-DOF movements of the tool head 24, i.e., X, Y, Z in the coordinate system, and pitch, roll and yaw. Fewer or additional DOFs may be present. For simplicity, only a generic illustration of the joints 22 and links 23 is provided, but more joints of different types may be present to move the tool head 24 in the manner described above. The joints 22 are powered for the robot arm 20 to move as controlled by the controller 50 in the six DOFs. Therefore, the powering of the joints 22 is such that the tool head 24 of the robot arm 20 may execute precise movements, such as moving along a single direction in one translation DOF, or being restricted to moving along a plane, among possibilities. Such robot arms 20 are known, for instance as described in U.S. patent application Ser. No. 11/610,728, incorporated herein by reference.

In FIG. 1, the tool head 24 supports a burr 26A, used to resurface a bone. As a non-exhaustive example, other tools that may be supported by the tool head 24 include a registration pointer, a reamer, a reciprocating saw, a retractor, a cut guide and the like, depending on the nature of the surgery. The various tools may be part of a multi-mandible configuration or interchangeable, whether with human assistance, or as an automated process. The installation of a tool in the tool head 24 may then require some calibration in order to track the installed tool in the X, Y, Z coordinate system of the robot arm 20.

In order to preserve the fixed relation between the leg and the coordinate system, and to perform controlled movements of the leg as described hereinafter, a generic embodiment is shown in FIG. 1. The foot support 30 may be displaceable relative to an operating room (OR) table, in order to move the leg in flexion/extension (e.g., to a fully extended position and to a flexed knee position), with some controlled lateral movements being added to the flexion/extension. Accordingly, the foot support 30 is shown as having a robotized mechanism by which it is connected to the OR table, with sufficient DOFs to replicate the flexion/extension of the lower leg. Alternatively, the foot support 30 could be supported by a passive mechanism, with the robot arm 20 connecting to the foot support 30 to actuate its displacements in a controlled manner in the coordinate system. The mechanism of the foot support 30 may have a slider 31, moving along the OR table in the X-axis direction. Joints 32 and links 33 may also be part of the mechanism of the foot support 30, to support a foot interface 34 receiving the patient's foot.

Referring to FIG. 1, the thigh support 40 may be robotized, static or adjustable passively. In the latter case, the thigh support 40 may be displaceable relative to the OR table, in order to be better positioned as a function of the patient's location on the table. Accordingly, the thigh support 40 is shown as including a passive mechanism, with various lockable joints to lock the thigh support 40 in a desired position and orientation. The mechanism of the thigh support 40 may have a slider 41, moving along the OR table in the X-axis direction. Joints 42 and links 43 may also be part of the mechanism of the thigh support 40, to support a thigh bracket 44. A strap 45 can immobilize the thigh/femur in the thigh support 40. The thigh support 40 may not be necessary in some instances. However, in the embodiment in which the range of motion is analyzed, the fixation of the femur via the thigh support 40 may assist in isolating joint movements.

Referring to FIG. 2, the robotized surgery controller 50 is shown in greater detail relative to the other components of the robotized surgery system 10. The controller 50 has a processor unit to control movement of the robot arm 20, and of the leg support (foot support 30 and thigh support 40), if applicable. The robotized surgery controller 50 provides computer-assisted surgery guidance to an operator, whether in the form of a range-of-motion (ROM) analysis or implant assessment in pre-operatively planning. Although not shown, the system 10 may comprise various types of interfaces, for the information to be provided to the operator. The interfaces may be monitors and/or screens including wireless portable devices (e.g., phones, tablets), audio guidance, LED displays, among many other possibilities. The controller 50 may then drive the robot arm 20 in performing the surgical procedure based on the planning achieved pre-operatively. The controller 50 may do an intra-operative soft-tissue balancing assessment, and hence enable corrective plan cuts to be made, or guide the selection of implants. The controller 50 may also perform a post-operative ROM analysis. The robotized surgery controller 50 runs various modules, in the form of algorithms, code, non-transient executable instructions, etc, in order to operate the system 10 in the manner described herein.

The controller 50 may hence have a robot driver module 51. The robot driver module 51 is tasked with powering or controlling the various joints of the robot arm 20, foot support 30 and thigh support 40, if applicable. As shown with bi-directional arrows in FIG. 2, there may be some force feedback provided by the robot arm 20 and leg support 30, to avoid overextending the leg and/or damaging the soft tissue. The robot driver module 51 may control the foot support 30 in performing particular motions, to replicate a flexion/extension of the knee, with lateral movements, to measure soft tissue tension and analyze the range of motion of the leg, including varus/valgus. As such, the robot driver module 51 may output the instant angle of flexion using the position and/or orientation data it uses to drive the movement of the foot support 30. Sensors 35 are provided on the foot support 30 in order to measure throughout the movement the forces indicative of the tension/stress in the joint. The sensors 35 must therefore be sensitive enough to detect soft tissue tension/stress through the movement of the foot support 30.

A force measurement module 52 receives the signals from the sensors 35, and calculates the instant forces in the foot support 30, representative of the tension/stress in the knee joint. The instant forces are received by a ROM analysis module 53, along with the foot support tracking data from the robot driver module 51. In the latter case, other tracking technology may be used to determine the instance flexion/extension and varus/valgus, such as optical tracking, inertial sensors, etc. With the combined data from the force measurement module 52 and from the robot driver module 51 or other source, the ROM analysis module 53 may produce a ROM analysis. The information of the ROM analysis may therefore be a pre-operative indication of the current varus/valgus as a function of flexion/extension. The ROM analysis module 53 may also be used in similar fashion post-operatively, to quantify the soft tissue balancing resulting from surgery.

The implant assessment module 54 determines how an implant or implants will impact the range of motion. Using the ROM analysis from the ROM analysis module 53, the implant assessment module 54 takes into consideration the geometrical configuration of the implants based on selectable locations on the bone, to perform the assessment. For example, the implant assessment module 54 may have the bone models 60 from pre-operative imaging (e.g., MRI, CT-scans), whether in 3D or in multiple 2D views. In a preferred embodiment, the bone models are generated via a 2D X-ray to 3D bone model process, such as described in U.S. Patent Application Publication Nos. 2016/0089153, filed on Sep. 25, 2014, and 2011/0305379, filed on Feb. 2, 2010, the contents of which are hereby incorporated by reference. The implant assessment module 54 may also have the implant models 61, such as the 3D model files including implants of different dimensions.

The implant assessment module 54 may be fully automated, in evaluating from the bone models 60, implant models 61 and/or from the ROM analysis desired implant sizes and location on the bone (i.e., in position and orientation), to balance soft tissue tension/stress. The information of the implant assessment may therefore be a pre-operative indication of an anticipated post-surgical varus/valgus as a function of flexion/extension. In such an embodiment, the implant assessment module 54 may provide the assessment to assist the operator in making a decision, as opposed to automatically proposing the desired implant sizes and location on the bone. The proposal of desired implant sizes and location on the bone may be a starting point of operator navigation or decision making. When the implant sizes and location on the bone is selected or set, the implant assessment module 54 may produce an output 62 in any appropriate format.

The output 62 may also include bone alteration data to assist the operator or the robot arm 20 in performing the bone alterations. In such a case, a resurfacing evaluation module 55 may calculate the bone cut volume and location, for the bone cuts that will be made based on the implant sizes and location on the bone.

The output 62 may also be a navigation file for the robot arm 20 to perform bone alterations based on the pre-operative planning from the implant assessment module 54. The navigation file would be patient-specific numerical control data defining the maneuvers to be performed by the robot arm 20 as directed by the robot driver 51 of the system 10, or of another system 10 in an operating room. The navigation file for robotized surgery may incorporate a calibration sub-file to calibrate the robot arm 20 and patient joint prior to commencing surgery. For example, the calibration sub-file may include the bone models 60 of the patient, for surface matching and registering to be performed by a registration pointer of the robot arm 20. The robot arm 30 would obtain a cloud of bone landmarks of the exposed bones, to reproduce a 3D surface of the bone. The 3D surface would then be matched to the bone models 60 of the patient, to set the 3D model in the X, Y, Z coordinate system.

In another embodiment, the output 62 is in the form of a patient-specific cut guide 3D file, for a patient-specific cut guide to be machined or 3D printed for operative use. For example, the patient-specific cut guide may have negative surfaces of the bone models 60 for unique positioning on the bone, such that cut planes and drill guides are placed as planned. As another example, the output 62 may be a navigation file, of the type programmed into inertial sensor units manually navigated by an operator.

Referring back to FIG. 1, the OWM system 70 has an optical device 80, a multicore optical waveguide 90 optically coupled to the optical device 80 and a processing unit 100 communicatively coupled to the optical device 80. The processing unit 100 is shown as part of the optical device 80, but could also be standalone, or part of the robotized surgery controller 50. As shown in this example, the multicore optical waveguide 90 is provided in the form of a multicore optical fiber 92. In some other embodiments, however, the multicore optical waveguide 90 may be provided in the form of a multicore strip waveguide and the like.

In this embodiment, the optical device 80 is configured for transmitting optical signals along the multicore optical fiber 92 and for receiving return optical signals from the multicore optical fiber 92. Further, the optical device 80 is configured to transmit electric signals to the processing unit 100, the electric signals being representative of the received return optical signals. Based on the received electric signals, the processing unit 100 is adapted and configured to generate a three-dimensional waveguide model representing the shape and orientation of the multicore optical fiber 92 at a specific moment in time. For instance, FIG. 3 shows a plot of a waveguide model 63 generated by the processing unit 100, which represents the multicore optical fiber 92 shown in FIG. 1.

Accordingly, by monitoring the waveguide model over time, the OWM system 70 allows the monitoring of the shape and the orientation of the multicore optical fiber 92 in real time or quasi real time. In some embodiments, the OWM system 70 generally has a small footprint and is lightweight, which can provide the ability to track instruments such as the tool head 24, bones and limbs, with a millimeter-level accuracy.

As depicted, the OWM system 70 has one multicore optical fiber 92, having for example a diameter of 200 microns and has an axial length up to a few meters. However, in some other embodiments, the OWM system 70 can have more than one multicore optical fiber, with different diameters and/or different axial lengths.

FIG. 4 shows a portion of the multicore optical fiber 92 of FIG. 1. As depicted, the multicore optical fiber 92 has three cores 93a, 93b, 93c which extend along an axial length l of the multicore optical fiber 92. In some other embodiments, the multicore optical fiber 92 can have more than three cores. For instance, the multicore optical fiber 92 can have four cores.

In this example, the cores 93a, 93b and 93c are embedded in an inner cladding 98a. The inner cladding 98a generally has a refractive index which is lower than a refractive index of each one of the cores 93a, 93b and 93c. The refractive index of the cores 93a, 93b and 93c need not to be identical from one core to another. The multicore optical fiber 92 has an outer cladding 98b surrounding the inner cladding 98a. Moreover, the multicore optical fiber 92 can be provided with a sheath covering the outer cladding 98b, for at least some providing mechanical resistance to the multicore optical waveguide 92.

As depicted, the cores 93a, 93b and 93c are off-axis and circumferentially spaced-apart from one another. In this example, the cores 93a, 93b and 93c are circumferentially spaced-apart by 60°. It is contemplated that the cores 93a, 93b and 93c are sufficiently spaced-apart from one another to prevent cross-talk between the cores 93a, 93b and 93c. In this specific example, each core 93a, 93b, 93c is sized and shaped to be single-mode for light having a wavelength of 1550 nm. In alternate embodiments, however, each core may be sized and shaped to be multimode.

The OWM system 70 involves distributed strain measurements in each of the cores 93a, 93b and 93c of the multicore optical fiber 92, at different axial positions $l_i$ along its axial length l, to construct the waveguide model 63. In this example, i is an integer ranging from 1 and a number N of axial positions. The axial increment $\Delta l$ between two successive axial positions $l_i$ can be in the order of the millimeter for example. The axial increments $\Delta l$ between successive axial positions $l_i$ need not be identical for each pair of successive axial positions $l_i$ where strain measurements are taken.

To measure strain in a unicore waveguide, light is sent down the core of the waveguide, where wavelengths of the reflected light are a function of the strain on the core and its temperature. To reduce the effect of temperature, the sheath of the multicore optical fiber can provide thermal insulation. In the context of the multicore optical fiber 92, however, bending of the multicore optical fiber 92 induces strain on each one of the cores 93a, 93b and 93c, which can be measured by monitoring the reflected wavelengths from each core 93a, 93b, 93c. The induced strains are a function of the local degree of bending of the multicore waveguide fiber 92. For instance, more strain is induced in the multicore optical fiber 92 around its elbow portion than in any of its straight portions.

The cores 93a, 93b and 93c allow at least two non-coplanar pairs of cores to be formed. For instance, in this embodiment, the cores 93a and 93b form a first pair 94a of cores lying in a first plane 95a, and the cores 93a and 93c form a second pair 94b of cores lying in a second plane 95b that is not coplanar with the first plane 95a. As having only the first pair 94a of cores would allow reconstruction of the bending of the corresponding waveguide only in the first plane 95a, having the two non-coplanar pairs 94a and 94b of cores can allow reconstruction of the bending of the corresponding waveguide in both the first and second planes 95a and 95b, thus allowing a three dimensional model of the multicore optical fiber 92 to be determined.

For instance, a first strain measurement at a first axial position $l1$ in the first core 93a can be compared to a second strain measurement at the first axial position $l1$ in the core 93b to determine a relative strain in the first plane 95a comprising the first pair 94a of cores. Similarly, the first strain measurement can be compared to a third strain measurement at the first axial position $l1$ in the core 93c to determine a relative strain in the second plane 95b comprising the second pair 94b of cores.

By doing so, the processor unit 100 combines the relative strains in the first and second planes 95a and 95b and arrives with a strain distribution in the multicore optical fiber 92 at the first axial position $l1$. Then, a strain distribution of the multicore optical fiber 92 at a second axial position $l2$ along the multicore optical fiber 92 is determined. By comparing the strain distributions at the first and second axial positions $l1$ and $l2$, the shape and orientation of the multicore optical fiber 92 between the first and second axial positions $l1$ and $l2$ can be determined by the processor unit 100. The strain distribution is then determined at a third axial position $l3$ along the multicore optical fiber 92, which can be used to determine the shape and orientation of the multicore optical fiber 92 between the second and third axial positions $l2$ and 13, and so forth, until the shape and orientation of the whole multicore optical fiber 92 is determined.

In this embodiment, such distributed strain measurements are based on fiber Bragg gratings (FBGs) 96. Broadly described, each FBG 96 comprises a series of modulations of the refractive index of the corresponding core to generate a spatial periodicity in the refraction index. The spacing of the modulations is chosen so that each index change causes reflection of a narrow band of wavelengths, and lets other wavelengths pass through. During fabrication of the FBG, the modulations are spaced by a known distance, thereby causing reflection of a known band of wavelengths, which is generally referred to as the Bragg wavelength. However, when a strain is induced on any one of the cores 93a, 93b and 93c, the spacing of the modulations can change depending on the amount of strain in the corresponding core, and so does the Bragg wavelength of the corresponding FBG 96.

Accordingly, in this embodiment, each core 93a, 93b, 93c of the multicore optical fiber 92 has an array of FBGs 96 inscribed at different axial positions li along their respective axial lengths. If located at axial positions li where the multicore optical fiber 92 is bent, the FBGs 96 can thereby be used to determine the amount of bending at those axial positions li. The strain measurements, combined with the known spacing distances between each FBG 96, can be used to reconstruct the waveguide model 63.

Such distributed strain measurements can also be based on inherent backscattering in any one of the cores 93a, 93b and 93c, also known as Rayleigh backscattering. In this embodiment, the optical signals received from the cores of the multicore optical fiber includes Rayleigh scattering or any other suitable type of backscattering. Rayleigh scatter occurs as a result of defects distributed along the cores of the multicore optical fiber causing random fluctuations of the refractive index in each of the cores of the multicore optical fiber. These random fluctuations can result in localized reflective interfaces which can reflect more or less some wavelengths along the cores of the multicore optical fiber. By monitoring such backscattering from each core of the multicore optical fiber, distributed strain measurements can also be performed. For various reasons, including consistency, predictability and reflectivity, fiber Bragg gratings 96 are generally preferred over such Rayleigh backscattering techniques.

Many ways of interrogating the FBGs 96 and distinguishing the readings from each FBG 96 exist and can be used by the processing unit 100. In some embodiments, optical frequency domain reflectometry (OFDR) can be used in which the FBGs 96, with the same grating period, are placed along each of the cores 93a, 93 b and 93c. Each core 93a, 93 b, 93c can be terminated with a partially reflecting mirror (not shown). The FBGs 96 are placed in such a way that the distance from each FBG 96 to the partially reflecting reflector is known, which causes the reflection spectrum of each FBG 96 to be modulated with a distinct modulation frequency, thereby allowing the individual reflection spectra to be determined. In addition, OFDR may be used to interrogate the array of FBGs 96 with sufficiently low delays such that that the bending data can be used as a feedback signal in a real-time motion control loop.

Sensors for determining a shape and orientation of a multicore optical fiber 92 have been used. For example, optical fibers including FBGs have been used in a variety of applications for providing strain measurements in multicore optical fibers. Examples of such systems are described in U.S. Patent Application Publication No. 2006/0013523, filed on Jul. 13, 2005, U.S. Provisional Patent Application Ser. No. 60/588,336, filed on Jul. 16, 2004, and U.S. Pat. No. 6,389,187, filed on Jun. 17, 1998. Examples of commercially available sensors for determining a shape and orientation of an optical fiber can be purchased from a variety of sources, such as Smart Fibres Ltd. of Bracknell, England, or Luna Innovations. Inc. of Blacksburg, Va.

Referring back to FIG. 1, the multicore optical fiber 92 has an ending portion 97a which is optically coupled to the optical device 80 and by which optical signals are transmitted and received.

The optical device 80, via the processing unit 100, is used to measure the distributed strain measurements from the multicore optical fiber 92. More specifically, the optical device 80 can include one or more optical sources, one or more optical detectors, electrical connections, optical waveguides such as fibers, optical couplers and the like so as to send optical signal in the cores 93a, 93b and 93c of the multicore optical fiber 92 and receive optical signals therefrom, from which the distributed strain measurements can be determined.

Robot arm attachments 110 can be used to attach different portions of the multicore optical fiber 92 to the links 23 and to the tool head 24 of the robot arm 20. More specifically, portions 97b, 97c and 97d of the multicore optical fiber 92 are attached to corresponding links 23 and portion 97e of the multicore optical fiber 92 is attached to the tool head 24. In an embodiment, the joints 22 of the robot arm 20 have position encoders or sensors such that the controller 50 may track the position of each point along the robot arm without attaching the multicore optical fiber 92 to the links 23. In such an embodiment, the multicore optical fiber 92 need only be attached to the robot arm 20 at the tool head 24 in order to implement tracking of the lower leg and thigh of the patient in the X, Y, Z coordinate system, as described herein. An example of such a robot arm is the TX60 industrial robot of Staubli Robotics of Faverges, France.

Limb attachments 120a and 120b are used to attach different portions of the multicore optical fiber 92 to a respective one of the lower leg (e.g., tibia) and the thigh (e.g., femur) of the patient. More specifically, portion 97f of the multicore optical fiber 92 is attached to the lower leg of the patient and portion 97g of the multicore optical fiber 92 is attached to the thigh of the patient.

The limb attachments 120a and 120b attached to the patient need not be invasively anchored to the bone, as straps or like attachment means can provide sufficient grasping to prevent movement between the limb attachments 120a and 120b, the corresponding portion of the multicore optical fiber 92 and the bones, in spite of being attached to soft tissue. However, in some other embodiments, the limb attachments 120a and 120b are provided in the form of bone attachments which are invasively anchored to the bones.

As illustrated in FIG. 2, the controller 50 has a model registration module 57 which receives the waveguide model 63 generated by the OWM system 70 and registers the waveguide model 63 in the X, Y, Z coordinate system.

The waveguide model 63 can be registered in the X, Y, Z coordinate system based on the known spatial relationship between the tool head 24 in the X, Y, Z coordinate system and on the known spatial relationship between the portion 97e of the multicore optical fiber 92 to which the tool head 24 is attached.

To do so, an input 64 representative of the known spatial relationship between the portion 97e of the multicore optical fiber 92 and the tool head 24 can be provided to the model registration module 57 subsequently to the attachment of the multicore optical fiber 92 to the tool head 24.

As can be understood, the bone models 60 may not be generated in the X, Y, Z coordinate system and the spatial relationship of the tool head 24 with respect to the bone model 60 is unknown a priori. Accordingly, the model registration module 57 receives the bone models 60 and registers the bone models 60 in the X, Y, Z coordinate system based on the waveguide model 63 and the known spatial relationship between the portions 97f and 97g of the multicore optical fiber 92 which are attached to the lower leg and to the thigh of the patient. The known spatial relationship between the multicore optical fiber 92 and the patient can be obtained through a calibration process, an example of which is described with reference to FIGS. 6-8 below.

As shown in FIG. 2, the input 64 provided to the model registration module 57 can include information concerning the known spatial relationship between the portions 97f and 97g of the multicore optical fiber 92 and each of the lower leg and the thigh of the patient, and associated bones.

As can be understood, the model registration module 57 can register the bone models 60 in the X, Y, Z coordinate system based on the waveguide model 63. In this way, the model registration module 57 performs the calibration of the bones of the patient with respect to the tool head 24, for subsequent navigation in the X, Y, Z coordinate system during surgery. Therefore, the controller 50 can continuously update the position and orientation of the tool head 24 and of the bones of the patient in the X, Y, Z coordinate system using successive waveguide models 63 generated by the OWM system 70. It will be appreciated that the controller 50 can update the position and orientation of the bones of the patient in the X, Y, Z coordinate system by using a multicore optical fiber tethered to the bones, therefore avoiding the need for rigid fixation of the bones during navigation.

FIG. 5 shows another example of an OWM system 70, in accordance with another embodiment. As shown in the illustrated embodiment, the OWM system 70 has an optical device 80 and a multicore optical fiber 92 optically coupled to the optical device 80, with the device 80 connected to or incorporating a processing unit 100. In this example, the multicore optical fiber 92 is provided with first and second bone attachments 120a and 120b, each being provided at known axial positions along the multicore optical fiber 92. The first and second bone attachments 120a and 120b can be used to attach corresponding portions of the multicore optical fiber 92 to one or more bones of the patient.

The multicore optical fiber 92 is also provided with first and second registration pointers 122a and 122b, each being provided at known axial positions along the multicore optical fiber 92. As will be described below, the first and second registration pointers 122a and 122b can be used to point to specific and highly recognizable areas of the bones, which can be determined using 2D X-ray to 3D bone model processes such as the ones discussed above. Meanwhile, the model registration module 57 (see FIG. 2) registers the shape and orientation of the waveguide model 63 with respect to the bone models 60 in the X, Y, Z coordinate system.

FIGS. 6-8 show different steps of a calibration method in the context of a knee surgery. As can be understood, in this example, the first bone attachment 120a can be a tibia attachment, the second bone attachment can be a femur attachment, the first registration pointer 122a can be a medial epicondyle registration pointer and/or a tibial tuberosity registration pointer, and the second registration pointer 122b can be a lateral epicondyle registration pointer.

FIG. 6 shows an image of the OWM system 70 of FIG. 5 in a first calibration step in which a previously obtained tibia model is registered in the X, Y, Z coordinate system. As shown, the multicore optical fiber 92 has an ending portion 94a being attached in a known spatial relationship with the tool head 24. A portion of the multicore optical fiber 92 is attached to the tibia using the first bone attachment 120a. A highly recognizable area of the tibia is pointed by the first registration pointer 122a, and a first waveguide model is generated in that position.

In this example, the first registration pointer 122a points to the tibial tuberosity of the tibia of the patient. As the first registration pointer 122a is assigned in the system 10 to register the recognizable area of the tibia of the patient, the bone model of the patient, and more specifically the tibia model, can be registered in the X, Y, Z coordinate system based on the first waveguide model. More specifically, the tibia model can be registered in the X, Y, Z coordinate system based on the first waveguide model, on the known geometry of the first registration pointer 122a and on the known spatial relationship between the first registration pointer 122a and the first bone attachment 120a along the multicore optical fiber 92. As can be seen, the multicore optical fiber 92 can have some slack 138 between the first registration pointer 122a and the first bone attachment 120a.

FIG. 7 shows an image of the OWM system 70 of FIG. 5 in a second calibration step in which a previously obtained femur model is registered in the X, Y, Z coordinate system. As depicted, a portion of the multicore optical fiber 92 is attached to the femur using the second bone attachment 120b. Two highly recognizable areas of the femur are pointed by each of the first and second registration pointers 122a and 122b, and a second waveguide model is generated in that position. As such, the two recognizable areas of the femur can be registered in the X, Y, Z coordinate system simultaneously.

In this example, the first registration pointer 122a points to the medial epicondyle of the femur while the second registration pointer 122b points to the lateral epicondyle of the femur of the patient. In this position, the femur model of the patient can be registered in the X, Y, Z coordinate system based on the second waveguide model as the first and second registration pointer 122a and 122b are assigned in the system 10 to register first and second recognizable area of the femur of the patient. Indeed, the femur model can be registered in the X, Y, Z coordinate system based on the second waveguide model, on the known geometry of the first and second registration pointers 122a and 122b and on the known spatial relationship between the first and second registration pointers 122a and 122b and the second bone attachment 120b along the multicore optical fiber 92. As can be seen, the multicore optical fiber 92 can have some slack 138 between the first registration pointer 122a and the first bone attachment 120a and some slack 138 between the first bone attachment 120a and the second registration pointer 122b.

When these steps are performed, both the tibia model and the femur model can be registered in the X, Y, Z coordinate system. After such calibration, e.g., during surgery, further movements of the tibia and/or femur of the patient can be tracked by tracking corresponding movements of the multicore optical fiber 92.

Referring back to FIG. 5, there is shown a cut plane validation tool 130. As depicted, the cut plane validation tool 130 has a known geometry with two opposite ends 132a and 132b. One of the ends 132a and 132b has a base 134 whereas the other one of the ends 132a and 132b has a planar surface 136 on which is attached a given length of the multicore optical fiber 92. More specifically, the given length of the multicore optical fiber 92 has an arcuate portion 137 extending in a plane of the planar surface 136. As can be understood, the cut plane validation tool 130 can help in validating cut made in surgery in some embodiments and/or determining cut planes in the X, Y, Z coordinate system using the waveguide model 63 in some other embodiments.

FIG. 8 shows an image of the OWM system 70 of FIG. 5 in a further calibration step in which some cut planes are registered in the X, Y, Z coordinate system. As depicted, the base 134 of the cut plane validation tool 130 can be positioned on one or more desired cut planes with respect to the tibia and/or the femur of the patient, and corresponding waveguide model(s) can be generated. Based on these waveguide models and more specifically on the model of the arcuate portion 137 of the multicore optical fiber 92 in the X, Y, Z coordinate system, on the known geometry of the cut plane validation tool 130, the desired cut plane(s) can be registered in the X, Y, Z coordinate system.

FIG. 9 shows a schematic view of the OWM system 70 in a further calibration step in which a patella 140 of the patient is registered and tracked in the X, Y, Z coordinate system. In this embodiment, the multicore optical fiber 92 has additional length beyond the second bone attachment 120b depicted in FIG. 5. As shown in FIG. 9A, the surgeon can tightly wrap this additional length around the patella 140 in a recognizable pattern and secure the additional length via a knot or clip 142 to the free end. A waveguide model is formed incorporating a series of arcuate portions formed by the multicore optical fiber 92 being wrapped tightly around the patella 140. Because of the multiple arcuate portions in the waveguide model, the OWM system 70 is able to recognize the geometry formed by the wrapping (resembling an 'X' in FIG. 9) as distinct from any other points along the model of the multicore optical fiber 92 ahead of attachment point 120b and can therefore register and track the position and orientation of the patella 140 without the use of an invasive tracking assembly. As will be understood, the multicore optical fiber 92 is wrapped around the patella 140 in a manner which prevents the multicore optical fiber 92 from breaking. In other words, arcuate portions 97h of the multicore optical fiber 92 are bent such that their radii of curvature do not exceed a given critical radius of curvature.

As can be understood, the examples described above and illustrated are intended to be exemplary only. For instance, the examples described above suggest that the waveguide model generated by the OWM system are registered in e.g., the X, Y, Z coordinate system of the tool head. However, in alternate embodiments, the waveguide model generated by the OWM system can be registered in an X', Y', Z' coordinate system of the bone models, in which the position and orientation of the tool head can also be registered. In another embodiment, the tool head to which is attached the multicore optical fiber need not to be mounted on a robot arm. Instead, the tool head, or any other surgical instrument, can be used in a manual surgical procedure operated by a surgeon. In this embodiment, for instance, registering the waveguide model in the X, Y, Z coordinate system can be useful to display the position of the tool with respect to the bones on a display. Moreover, as the illustrated embodiments show only a single multimode optical fiber, other embodiments can involve the use of two or more multimode optical fibers. The scope is indicated in the appended claims.

The invention claimed is:

1. A method for tracking a patient in a coordinate system of a surgical tool using an optical waveguide modeling system, the optical waveguide modeling system having at least one multicore optical fiber with at least one portion attached to the surgical tool and at least one portion attached to the patient, the method comprising:

using a controller,
receiving a patient model representing a shape and orientation of at least one of a limb and a bone of the patient;
generating a waveguide model representing a shape and orientation of the multicore optical fiber as attached to the surgical tool and to the patient; and
tracking the patient model in the coordinate system of the surgical tool by registering the patient model in the coordinate system of the surgical tool using the waveguide model, a known spatial relationship between the surgical tool and the at least one portion of the multicore optical fiber attached to the surgical tool and a known spatial relationship between the patient and the at least one portion of the multicore optical fiber attached to the patient.

2. The method of claim 1 wherein the waveguide model is generated when a registration pointer attached to a known portion of the multicore optical fiber points to a specific and recognizable area of the patient.

3. The method of claim 2, wherein a first registration pointer attached to a first known portion of the multicore optical fiber is assigned in the optical waveguide modeling system to register a recognizable area of a tibia of the patient.

4. The method of claim 3, wherein a second registration pointer attached to a second known portion of the multicore optical fiber is assigned in the optical waveguide modeling system to register a first recognizable area of a femur of the patient.

5. The method of claim 4, wherein the first registration pointer is also assigned in the optical waveguide modeling system to register a second recognizable area of the femur of the patient.

6. The method of claim 5, wherein said tracking the patient model in the coordinate system of the surgical tool by registering the patient model in the coordinate system of the surgical tool using the waveguide model includes using the first and second registration pointers to simultaneously register the first and second recognizable areas of the femur of the patient.

7. The method of claim 6, wherein the first and second recognizable areas on the femur of the patient are a respective one of a lateral epicondyle and a medial epicondyle.

8. The method of claim 1, wherein the surgical tool comprises a tool head of a robot arm of a robotized surgical system.

9. The method of claim 1, further comprising validating a cut made in surgery with a cut plane validation tool having a known geometry and attached to a known portion of the multicore optical fiber.

10. A computer-assisted surgery system for tracking a tool with respect to a bone of a patient, comprising:
a patient model representing a shape and orientation of the bone of the patient;
a surgical tool in communication with the computer-assisted surgery system;
an optical waveguide modeling system having a multicore optical fiber;
one or more limb attachments provided at one or more known positions along the multicore optical fiber; and
one or more registration pointers provided at one or more known positions along the multicore optical fiber.

11. The system of claim 10, further comprising a cut plane validation tool attached to the multicore optical fiber.

12. The system of claim 11, wherein the cut plane validation tool comprises a planar surface and the multicore optical fiber has an arcuate portion extending in a plane of the planar surface.

13. The system of claim 10, wherein a single multicore optical fiber is used to track positions of the surgical tool and of the bone of the patient.

14. The system of claim 13, wherein the optical waveguide modeling system is configured to register at least two distinct recognizable areas simultaneously identified by two or more registration pointers provided at known positions along the multicore optical fiber.

15. The system of claim 10, wherein the surgical tool comprises a tool head of a robot arm of a robotized surgical system.

16. The system of claim 15, further comprising an optical device communicatively coupled to a robotized surgery controller and configured for interrogating a plurality of Bragg gratings spatially-spaced apart from one another along cores of the multicore optical fiber.

17. The system of claim 16, wherein a second registration pointer is located on the multicore optical fiber at a position between the optical device and the one or more of the limb attachments.

18. The system of claim 17, wherein at least one of the one or more registration pointers is configured to register a specific point on a highly recognizable area of the bone.

19. The system of claim 10, wherein a first registration pointer is located on the multicore optical fiber at a position between a first limb attachment and a second limb attachment along the multicore optical fiber.

20. The system of claim 10, wherein the patient model is based on a 2D X-ray to 3D process.

21. The system of claim 10, further comprising a series of arcuate portions formed by the multicore optical fiber being wrapped around a patella of the patient.

* * * * *